(12) United States Patent
Locke (10) Patent No.: US 12,070,377 B2
(45) Date of Patent: Aug. 27, 2024

(54) CONNECTION ASSEMBLY WITH PERFORATED FILM LAYER FOR ABSORBENT NEGATIVE PRESSURE DRESSING

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

(*) Notice: Subject to any disclaimer, the term of this patent is extended or adjusted under 35 U.S.C. 154(b) by 130 days.

(21) Appl. No.: 17/606,516

(22) PCT Filed: May 14, 2020

(86) PCT No.: PCT/US2020/032875
§ 371 (c)(1),
(2) Date: Oct. 26, 2021

(87) PCT Pub. No.: WO2020/232239
PCT Pub. Date: Nov. 19, 2020

(65) Prior Publication Data
US 2022/0203017 A1 Jun. 30, 2022

Related U.S. Application Data

(60) Provisional application No. 62/848,958, filed on May 16, 2019.

(51) Int. Cl.
*A61F 13/05* (2024.01)
*A61F 13/00* (2024.01)
(Continued)

(52) U.S. Cl.
CPC ........ *A61F 13/05* (2024.01); *A61F 13/00055* (2013.01); *A61F 13/0206* (2013.01);
(Continued)

(58) Field of Classification Search
CPC ............. A61F 13/0206; A61F 13/0216; A61F 13/0289; A61F 13/00055; A61F 13/00068;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Leslie A Lopez
*Assistant Examiner* — Timothy L Flynn (57) ABSTRACT

An assembly for coupling a dressing to a tube connected to a pump includes a hydrophobic film layer comprising a perforation extending therethrough, an indicator coupled to a first side of the hydrophobic film layer and positioned proximate the perforation, a felted foam layer coupled to a second side of the hydrophobic film layer and fluidly communicable with the indicator via the perforation, and a connection pad coupled to the first side of the hydrophobic film layer and coupleable to the tube.

20 Claims, 6 Drawing Sheets

(51) Int. Cl.
    *A61F 13/02* (2024.01)
    *A61F 13/0206* (2024.01)
    *A61M 1/00* (2006.01)

(52) U.S. Cl.
    CPC ......... *A61F 13/0289* (2013.01); *A61M 1/912* (2021.05); *A61M 1/915* (2021.05); *A61M 1/985* (2021.05); *A61M 1/966* (2021.05); *A61M 1/982* (2021.05); *A61M 2207/00* (2013.01)

(58) Field of Classification Search
    CPC .. A61F 13/02; A61F 13/0203; A61F 13/0213; A61F 13/0223; A61F 13/025; A61F 13/0266; A61F 13/0256; A61M 1/912; A61M 1/982; A61M 1/985; A61M 1/966; A61M 2207/00
    See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0227969 A1* | 9/2009 | Jaeb ................ A61F 13/00068 604/313 |
| 2014/0163491 A1 | 6/2014 | Schuessler et al. |
| 2015/0080788 A1 | 3/2015 | Blott et al. |
| 2018/0303967 A1* | 10/2018 | Quintero ................ A61L 15/58 |
| 2019/0133830 A1* | 5/2019 | Bishop .............. A61F 13/00068 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2018226667 A1 | 12/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2020/032875 mailed Aug. 24, 2020.

* cited by examiner

CONNECTION ASSEMBLY WITH PERFORATED FILM LAYER FOR ABSORBENT NEGATIVE PRESSURE DRESSING

CROSS-REFERENCE TO RELATED APPLICATIONS

This application claims the benefit of priority to U.S. Provisional Application No. 62/848,958, filed on May 16, 2019, which is incorporated herein by reference in its entirety.

BACKGROUND

The present disclosure relates generally to the field of wound therapy, and more particularly to dressings for use in negative pressure wound therapy.

Negative pressure wound therapy (NPWT) is a type of wound therapy that involves applying negative pressure (relative to atmospheric pressure) to a wound bed to promote wound healing. Typically, a dressing is sealed over a wound bed and air is pumped out of the dressing to create a negative pressure at the wound bed. In some NPWT systems, wound exudate and other fluid is pumped out of the dressing and collected by a therapy system.

In other NPWT systems, air is pumped out of the dressing while the dressing is used to absorb fluid from the wound. In some such systems, it is preferable for air to be drawn to the pump while fluid or other wound exudate is prevented from reaching the pump, such that the pump is protected from contamination or other damage that may be caused by such fluid or other exudate contacting the pump. Accordingly, assemblies for protecting the pump from contact with fluid or other wound exudate while also allowing the pump to remove air from the dressing are needed.

SUMMARY

One implementation of the present disclosure is an assembly for coupling a dressing to a tube connected to a pump. The assembly includes a hydrophobic film layer comprising a perforation extending therethrough, an indicator coupled to a first side of the hydrophobic film layer and positioned proximate the perforation, a felted foam layer coupled to a second side of the hydrophobic film layer and fluidly communicable with the indicator via the perforation, and a connection pad coupled to the first side of the hydrophobic film layer and coupleable to the tube.

In some embodiments, the felted foam layer is fluidly communicable with the connection pad via the perforation. In some embodiments, the indicator is configured to change colors in response to contacting fluid. In some embodiments, the indicator includes a hydrochromic layer that includes a hole extending therethrough, the hole aligned with the perforation.

In some embodiments, the assembly includes an adhesive layer configured to couple the indicator to the hydrophobic film layer. The adhesive layer includes a channel extending from the perforation to an edge of the indicator. The channel is configured to direct fluid from the perforation to the edge of the indicator. In some embodiments, the hydrophobic film layer is configured to allow the flow of air therethrough from the felted foam layer to the connection pad.

Another implementation of the present disclosure is a wound therapy system. The wound therapy system includes a wound contact layer configured to contact a wound, a manifolding layer coupled to a non-wound-facing side of the wound contact layer, and a drape coupled to the manifolding layer and sealable over the wound. The drape has a hole extending therethrough. The wound therapy system includes a felted foam layer positioned at the hole and fluidly communicable with the manifolding layer, and a hydrophobic film layer coupled to the felted foam layer and configured to allow air to flow therethrough and substantially prevent liquid from flowing therethrough. The hydrophobic film layer has a perforation extending therethrough. The perforation is configured to allow liquid to pass through the hydrophobic film layer. The wound therapy system includes a fluid-activated indicator coupled to the hydrophobic film layer proximate the perforation. The hydrophobic film layer is positioned between the fluid-activated indicator and the felted foam layer. The wound therapy system includes a connection pad coupled to the drape and sealed over the hole, the felted foam layer, the hydrophobic film layer, and the indicator, a tube coupled to the connection pad, and a pump coupled to the tube. The pump is operable to draw a negative pressure at the wound by removing air from the manifolding layer via the felted foam layer, the hydrophobic film layer, the connection pad, and the tube.

In some embodiments, the felted foam layer is fluidly communicable with the connection pad via the perforation. In some embodiments, the fluid-activated indicator is configured to change colors in response to contacting fluid. In some embodiments, the fluid-activated indicator includes a hydrochromic layer comprising a hole extending therethrough. The hole is aligned with the perforation.

In some embodiments, the wound therapy system includes an adhesive layer configured to couple the indicator to the hydrophobic film layer. The adhesive layer includes a channel extending from the perforation to an edge of the indicator. The channel is configured to direct fluid from the perforation to the edge of the indicator. In some embodiments, the connection pad is transparent or translucent such that the indicator is visible through the connection pad.

Another implementation of the present disclosure is a method for manufacturing a wound therapy system. The method includes coupling an indicator to a hydrophobic film layer, creating a perforation through the indicator and the hydrophobic film layer, coupling the hydrophobic film layer to a felted foam layer with the hydrophobic film layer positioned between the indicator and the felted foam layer, and coupling a connection pad to the hydrophobic film layer with the connection pad in fluid communication with the felted foam layer via the perforation.

In some embodiments, the method includes coupling the connection pad to a tube. In some embodiments, the method includes forming a hole through a drape, coupling the connection pad to the drape at the hole, coupling a manifolding layer to the drape with the manifolding layer fluidly communicable with the felted foam layer via the hole, and coupling a wound contact layer to the manifolding layer.

In some embodiments, the method includes coupling the connection pad to a tube and coupling the tube to a pump. The pump is configured to draw a negative pressure at the manifolding layer.

In some embodiments, the indicator comprises a hydrochromic layer configured to change color when the hydrochromic layer contacts fluid. In some embodiments, coupling the indicator to a hydrophobic film layer comprises providing an adhesive layer between the indicator and the hydrophobic film layer. In some embodiments, the method includes providing the indicator with a channel extending from the perforation to an edge of the indicator. In some embodiments, the method includes creating a plurality of additional perforations through the hydrophobic film layer.

DETAILED DESCRIPTION

Figure 1:
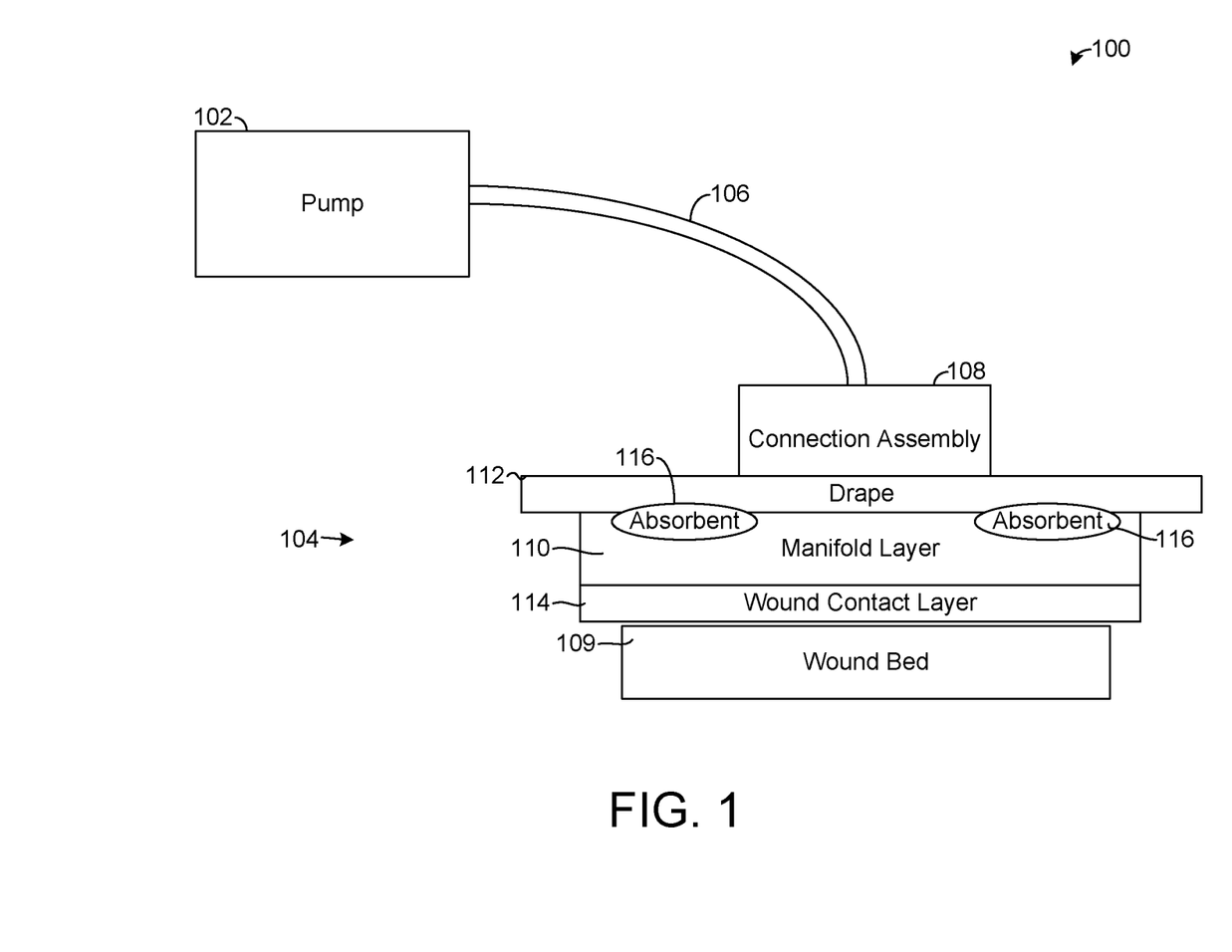
FIG. 1 is a block diagram of a negative pressure wound therapy (NPWT) system with an absorbent dressing, according to an exemplary embodiment.

Referring now to FIG. 1, a negative pressure wound therapy (NPWT) system 100 is shown, according to an exemplary embodiment. The NPWT system 100 includes a pump 102 pneumatically communicable with a dressing 104 via tube 106. The tube 106 is coupled to the dressing 104 by a connection assembly 108. The dressing 104 is shown as sealed over a wound bed 109. The wound bed 109 is a tissue wound of a patient, for example a laceration, burn, sore, trauma wound, chronic wound, etc.

The dressing 104 allows a negative pressure to be maintained at the wound bed 109 while absorbing fluid from the wound bed 109. The dressing 104 thereby provides both negative pressure and a high level of fluid absorption. The dressing 104 is shown to include drape 112, a manifold layer 110, a wound contact layer 114, and absorbent deposits 116. It should be understood that the dressing 104 is one example of an absorbent negative pressure dressing and that many embodiments are possible, for example as shown and described in U.S. Provisional Patent Application 62/732,285, filed Sep. 17, 2018, incorporated by reference herein in its entirety.

The drape 112 is configured to seal the wound contact layer 114, the manifold layer 110, and the absorbent deposits 116 over the wound bed 109. For example, the drape 112 may include an adhesive ring coupleable to the patient's skin surrounding the wound bed 109. The drape 112 may include a material that substantially prevents leaking of air therethrough to facilitate creation and maintenance of a negative pressure at the manifold layer 110 (i.e., in a volume between the drape 112 and the wound bed 109). The drape 112 may also include a material with a high moisture vapor transfer rate to facilitate evaporation of fluid from the absorbent deposits 116 to the ambient air through the drape 112.

The wound contact layer 114 provides an interface between the dressing 104 and a wound. In some embodiments, the wound contact layer 114 is configured to prevent ingrowth of the wound bed 109 to the dressing and to facilitate removal of the dressing 104 while minimizing damage to the healing tissue of the wound bed 109. The wound contact layer 114 includes a film, for example a silicone film. The wound contact layer 114 may be perforated or otherwise formed to allow for the flow of air and fluid therethrough.

The manifold layer 110 is configured to allow airflow therethrough to facilitate the distribution of negative pressure across the wound bed 109. In some embodiments, the manifold layer 110 may include an open-celled foam, for example a foam material marketed as GRANUFOAM™ by ACELITY™. The manifold layer 110 is also configured to allow fluid to flow therethrough, from the wound bed 109 to the absorbent deposits 116.

The absorbent deposits 116 are configured to absorb fluid, for example wound exudate from the wound bed 109. The absorbent deposits 116 may include a superabsorbent material. Various arrangements and configurations of the absorbent deposits 116 are included in various embodiments. In some embodiments, the absorbent deposits 116 are included as a superabsorbent laminate positioned between the drape 112 and the manifold layer 110, with channels extending therethrough to allow airflow therethrough. It should be understood that various configurations of absorbent dressings 104 are contemplated by the present disclosure and can be compatible with the connection assembly 108, which is described in detail with reference to FIGS. 2-7.

The connection assembly 108 is configured to couple the dressing 104 to a tube 106, which is coupled to a pump 102. As shown in FIGS. 2-7 and described in detail with reference thereto, the connection assembly 108 is configured to allow airflow between the manifold layer 110 and the pump 102, while restricting the flow of fluid therethrough and providing a visual indication when fluid passes therethrough.

The pump 102 is operable to pump air out of the dressing 104 via the tube 106 to create and maintain a negative pressure at the wound bed 109. In some embodiments, the pump 102 is electrically powered and the NPWT system 100 includes power systems and control circuitry to power and control operation of the pump 102. For example, the NPWT system 100 may include one or more pressure sensors or various other sensors that collect data used to control the pump 102 to maintain a negative pressure at the wound bed 109. In some embodiments, the pump 102 is manually-powered, such that a user may manipulate the pump 102 to draw air out of the dressing 104 as desired by the user. For example, the pump 102 may be spring-loaded to gradually pull air from the dressing 104 for a duration of time following a compression of the pump 102 by the user.

The NPWT system 100 is thereby configured to provide a negative pressure at the wound bed 109 while also facilitating absorption of fluid from the wound bed 109 by the dressing 104.

Figure 2:
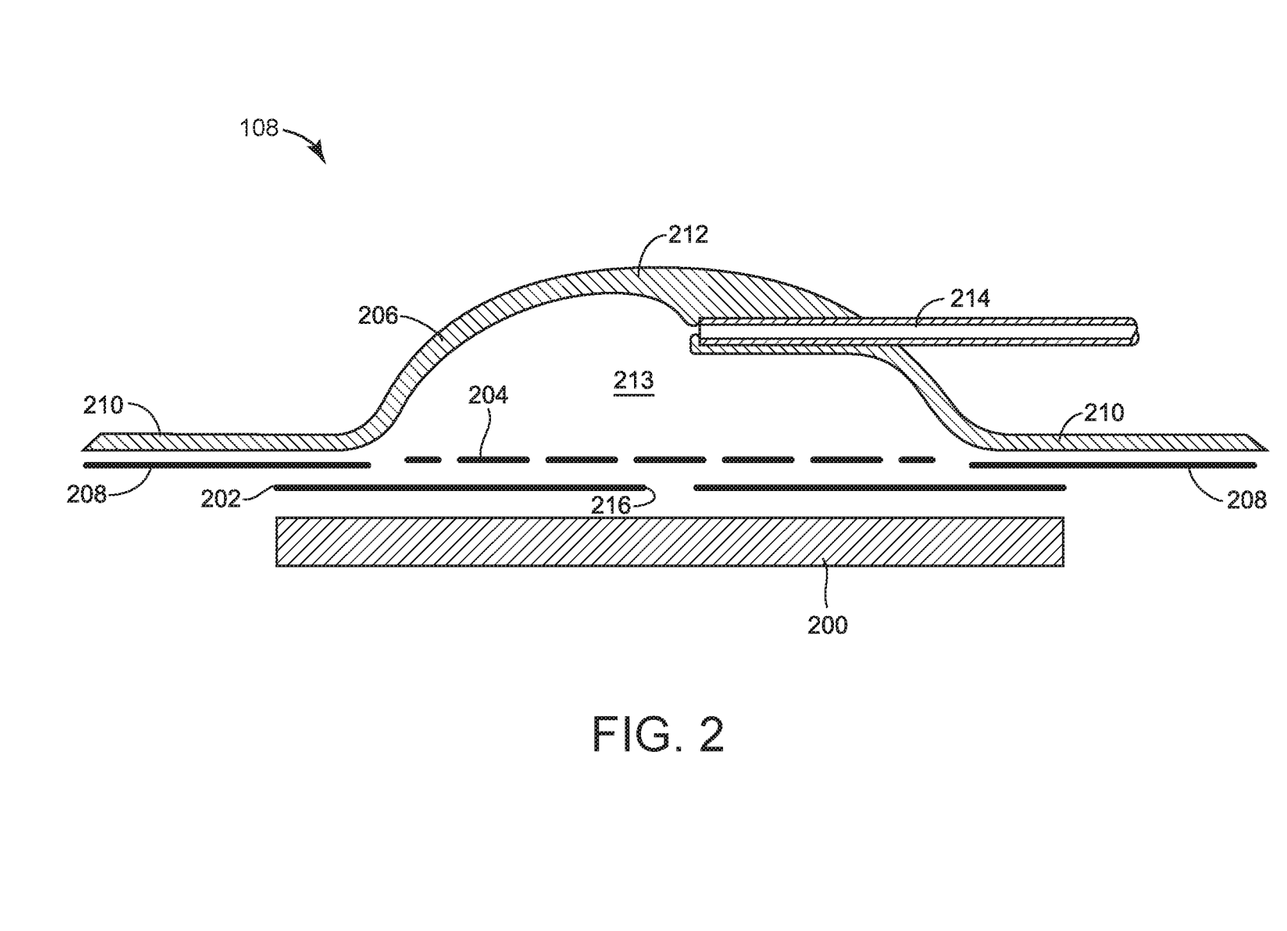
FIG. 2 is a cross-sectional diagram of a first embodiment of a connection assembly of the NPWT system of FIG. 1, according to an exemplary embodiment.

Referring now to FIG. 2, a cross-sectional view of a first embodiment of the connection assembly 108 of FIG. 1 is shown, according to an exemplary embodiment. The connection assembly 108 is configured to be positioned at a hole (opening, airway, channel) through the drape 112, such that the connection assembly 108 can be coupled to the drape 112 while in fluid communication with the manifold layer 110.

As shown in FIG. 2, the connection assembly includes a felted foam layer 200, a hydrophobic film layer 202 coupled to the felted foam layer 200, a fluid-activated indicator 204 coupled to the film layer 202, a connection pad 206 positioned over the felted foam layer 200, the hydrophobic film layer 202, and the fluid-activated indicator 204, and an adhesive ring 208 extending around a periphery of the connection pad 206.

The connection pad 206 includes a flat outer ring 210 and a center dimple 212 that extends from the outer ring 210 and away from the dressing 104. The connection pad 206 thereby defines a volume 213 between the center dimple 212 and a plane defined by the outer ring 210 (in the example shown, between the center dimple 212 and the fluid-activated indicator 204). The connection pad 206 includes a tube conduit 214 extending through the connection pad 206 at the center dimple 212. The tube conduit 214 is configured to couple the connection pad 206 to a tube 106 and place the tube 106 in fluid communication with the volume 213.

The adhesive ring 208 is positioned along the outer ring 210 and is configured to couple the outer ring to the drape 112 and the hydrophobic film layer 202. The adhesive ring 208 is configured to seal the connection assembly 108 to the drape 112, such that air and/or fluid is substantially prevented from leaking between the drape 112 and the connection assembly 108 to an ambient environment. In the example of FIG. 2, when the connection assembly 108 is coupled to the dressing 104, the volume 213 and the tube 106 are separated from the manifold layer 110 of the dressing 104 by the felted foam layer 200, the hydrophobic film layer 202, and the fluid-activated indicator 204.

The felted foam layer 200 is configured to allow airflow therethrough and to resist the flow of fluid therethrough such that fluid in the dressing 104 is directed to the absorbent deposits 116 or other wicking or absorbent structure of the dressing 104 when absorbent capacity is available in the dressing 104. The felted foam layer 200 thereby substantially prevents the flow of fluid into the connection assembly 108 when absorbent capacity is available in the dressing 104. When the dressing is full (i.e., when the absorbent capacity of the dressing 104 is met), the felted foam layer 200 is configured to allow fluid to pass therethrough from the manifold layer 110 to the hydrophobic film layer 202. Accordingly, passage of fluid through the felted foam layer 200 is associated with a full dressing 104. The felted foam layer 200 may include three to five times felted foam, where the foam is a same or similar foam as the manifold layer 110 (i.e., processed to be permanently compressed to a fraction of the original thickness of the foam material of the manifold layer 110).

The hydrophobic film layer 202 includes a hydrophobic film with one or more perforations extending therethrough. In FIG. 2, the hydrophobic film layer 202 is shown to include one perforation 216 positioned at approximately a center of the center dimple 212. The hydrophobic film prevents fluid from passing through the hydrophobic film, while the perforation 216 allows fluid to pass through the hydrophobic film layer 202. In some embodiments, the hydrophobic film includes a filter material that allows air to flow through the hydrophobic film while fluid is prevented from passing through the hydrophobic film. The perforation 216 allows air to flow therethrough, increasing the possible rate of airflow from the manifold layer 110 to the tube 106 relative to an alternative embodiment without a perforation 216. The one or more perforations 216 may be located centrally on the hydrophobic film layer 202, located towards or at an edge of the hydrophobic film layer 202, or otherwise poisoned on the hydrophobic film layer 202. The hydrophobic film layer 202 can include various micro-filter materials, micro-porous films, sintered polymers, etc.

Accordingly, when the dressing 104 has absorbed less than a maximum capacity of fluid, the felted foam layer 200 and the hydrophobic film layer 202 combine to substantially prevent a flow of fluid from the wound bed 109 to the volume 213. When the dressing 104 is full, i.e., when absorbent deposits 116 and the manifold layer 110 contain approximately a maximum possible amount of fluid, the felted foam layer 200 and the hydrophobic film layer 202 can allow fluid to flow through the felted foam layer 200 and the perforation 216 in the hydrophobic film layer 202 to reach the volume 213.

As shown in FIG. 1, the fluid-activated indicator 204 is positioned between the hydrophobic film layer 202 and the volume 213 (i.e., between the hydrophobic film layer 202 and the tube conduit 214). In the example of FIG. 2, the fluid-activated indicator 204 is formed as a layer of hydrochromic material having perforations extending therethrough, such that fluid can pass through the perforations from the hydrophobic film layer 202 to the volume 213. For example, the fluid-activated indicator 204 may include a water contact indicator tape, for example a tape marketed as 3M™ Water Contact Indicator Tape 5557 by 3M™. In other embodiments, the fluid-activated indicator 204 includes a dye that is painted, printed, or otherwise deposited on the hydrophobic film layer 202.

The fluid-activated indicator 204 is configured to change colors when fluid contacts the fluid-activated indicator 204 and/or release a dye when fluid contacts the fluid-activated indicator 204. The fluid-activated indicator 204 thereby provides a visual indication that fluid has passed through the hydrophobic film layer 202 to enter the volume 213. The connection pad 206 is transparent or translucent such that a change in color at the fluid-activated indicator 204 is visible through the connection pad (i.e., through the dimple 212).

The fluid-activated indicator 204 is thereby configured to provide a visual indication that allows a user to see when fluid has entered the volume 213 and/or when the dressing 104 is full of fluid. The fluid-activated indicator 204 may thereby facilitate protection of the pump 102 from wound exudate and other fluid by providing a warning to a user that fluid has reached the volume 213 where it could be drawn through the tube conduit 214 and the tube 106 to the pump 102. Accordingly, the visual indication provided by the fluid-activated indicator 204 may be used by a user in determining that the dressing 104 should be removed (i.e., in determining that a lifespan of the dressing 104 has ended), that the pump 102 should be disconnected, that some other modification to wound treatment should be made.

Figure 3:
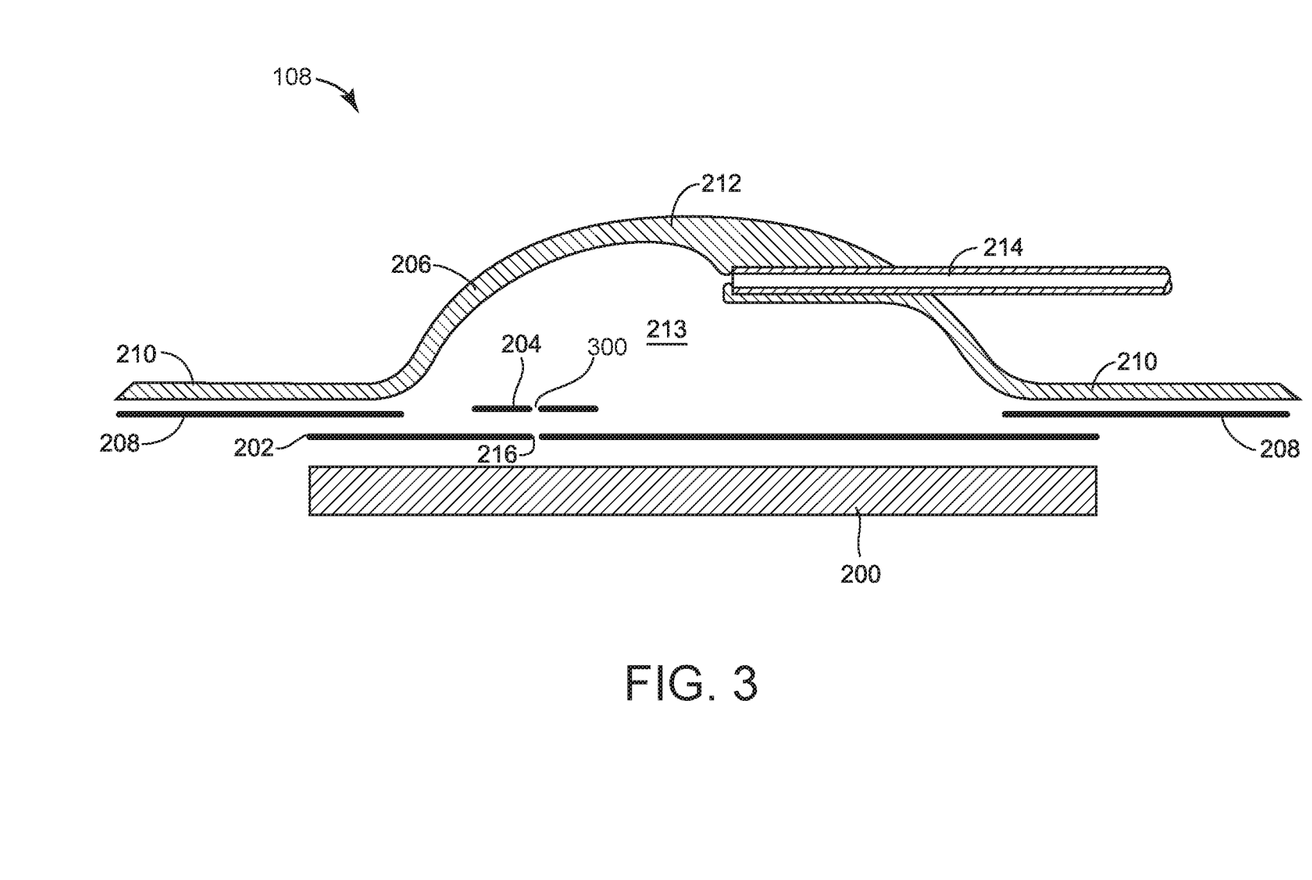
FIG. 3 is a cross-sectional diagram of a second embodiment of a connection assembly of the NPWT system of FIG. 1, according to an exemplary embodiment.

Referring now to FIG. 3, a second embodiment of the connection assembly 108 is shown, according to an exemplary embodiment. As in FIG. 2, the connection assembly 108 of FIG. 3 includes a felted foam layer 200, a hydrophobic film layer 202, a fluid-activated indicator 204, a connection pad 206, and an adhesive ring 208. The felted foam layer 200, the connection pad 206, and the adhesive ring 208, and the hydrophobic film layer 202 of FIG. 2 are substantially the same as described above with reference to FIG. 3.

As shown in FIG. 3, the hydrophobic film layer 202 includes the perforation 216. The perforation 216 of FIG. 3 is offset from a center of the dimple 212 of the connection pad 206. The perforation 216 may be various sizes in various embodiments, for example between 0.2 mm and 3 mm. Although a single perforation 216 is shown in FIG. 3, it should be understood that multiple perforations may extend through the hydrophobic film layer 202.

In the embodiment of FIG. 3, the fluid-activated indicator 204 is posited at the perforation 216 of the hydrophobic film layer 202. The fluid-activated indicator 204 is sized to cover only a portion of the hydrophobic film layer 202. The fluid-activated indicator 204 has a perforation 300 extending through the fluid-activated indicator 204. The perforation 300 of the fluid-activated indicator 204 is shown as aligned with the perforation 216 of the hydrophobic film layer 202. Alignment of the perforations 216, 300 allows air and/or fluid to flow through both perforations 300, 216 in series when moving between the felted foam layer 200 and the volume 213.

In some cases, the perforations 216, 300 are formed simultaneously during manufacturing of the connection assembly 108. That is, the fluid-activated indicator 204 can be coupled to the hydrophobic film layer 202 and then the perforations 216, 300 can be created through both fluid-activated indicator 204 and the hydrophobic film layer 202 in a single process, thereby ensuring alignment of the perforations 216, 300. The perforations 216, 300 can be manufactured by removing material, ablating material, deforming material, or atomizing the material, such that the material removed or deformed cannot become re-installed to close the perforations 216, 300. For example, the perforations can be formed with a laser, dye tool, punch, ultrasonics, etc. In some embodiments, radial ultrasonics are used to weld the hydrophobic film layer 202 and/or the fluid-activated indicator 204 to the felted foam layer 200. In such a case, the radial ultrasonics can be configured to also puncture the hydrophobic film layer 202 and/or the fluid-activated indicator 204 to create the perforation 216 and/or the perforation 300 as a by-product of the welding process.

Figure 4:
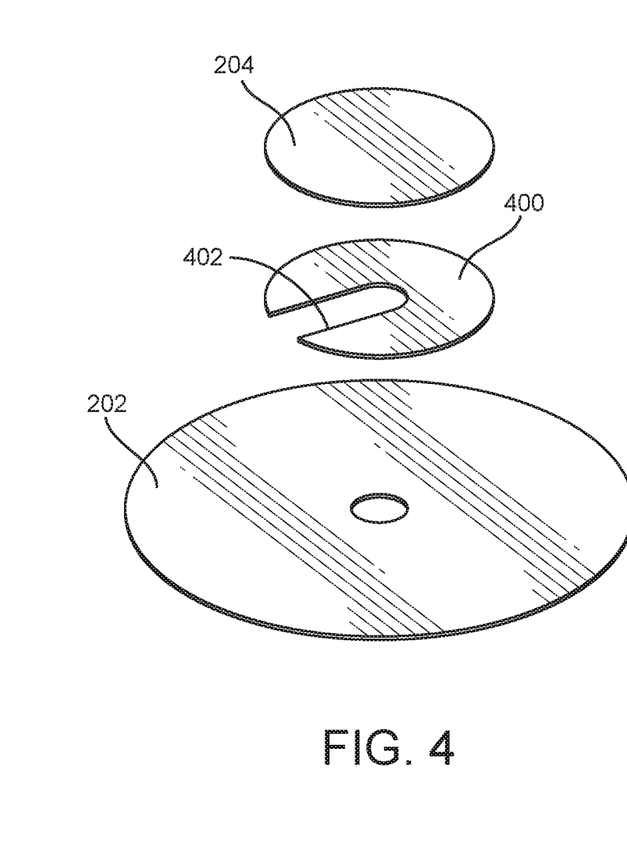
FIG. 4 is an exploded view of a portion of a third embodiment of a connection assembly of the NPWT system of FIG. 1, according to an exemplary embodiment.
Figure 5:
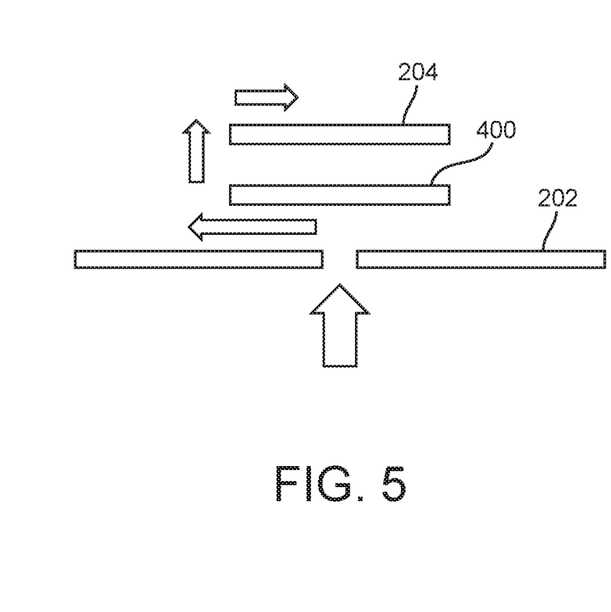
FIG. 5 is a cross-sectional view of the portion of the connection assembly of FIG. 4, according to an exemplary embodiment.

Referring now to FIGS. 4-5, a portion of a third exemplary embodiment of the connection assembly 108 is shown. FIG. 4 shows an exploded view of the hydrophobic film layer 202 and the fluid-activated indicator 204 with an adhesive layer 400. FIG. 5 shows a cross-sectional side view of the hydrophobic film layer 202 and the fluid-activated indicator 204 with the adhesive layer 400 of FIG. 4.

The adhesive layer 400 is configured to couple the fluid-activated indicator 204 to the hydrophobic film layer 202 proximate the perforation 216. In FIG. 4, the adhesive layer 400 has a circular shape that substantially matches a circular shape of the fluid-activated indicator 204 and is positioned between the fluid-activated indicator 204 and the hydrophobic film layer 202.

As illustrated in FIG. 4, the adhesive layer 400 includes a channel 402 extending from a center of the adhesive layer 400 to an edge of the adhesive layer 400 and to an edge of the fluid-activated indicator 204. The channel 402 is positioned over the perforation 216 such that the channel 402 is fluidly communicably with the perforation 216.

As illustrated in FIG. 5, when fluid flows through the perforation 216, the fluid enters the channel 402 and is directed along the channel 402 to an edge of the fluid-activated indicator 204. The fluid-activated indicator 204 substantially prevents the flow of fluid through the fluid-activated indicator 204. The channel 402 directs fluid into contact with a region of the fluid-activated indicator 204 aligned with the channel 402 from a center of the fluid-activated indicator 204 to an edge of the fluid-activated indicator 204, thereby activating that region of the fluid-activated indicator 204 (e.g., causing the corresponding region of the fluid-activated indicator 204 to change color). The channel 402 thereby facilitates activation of the fluid-activated indicator 204.

Figure 6:
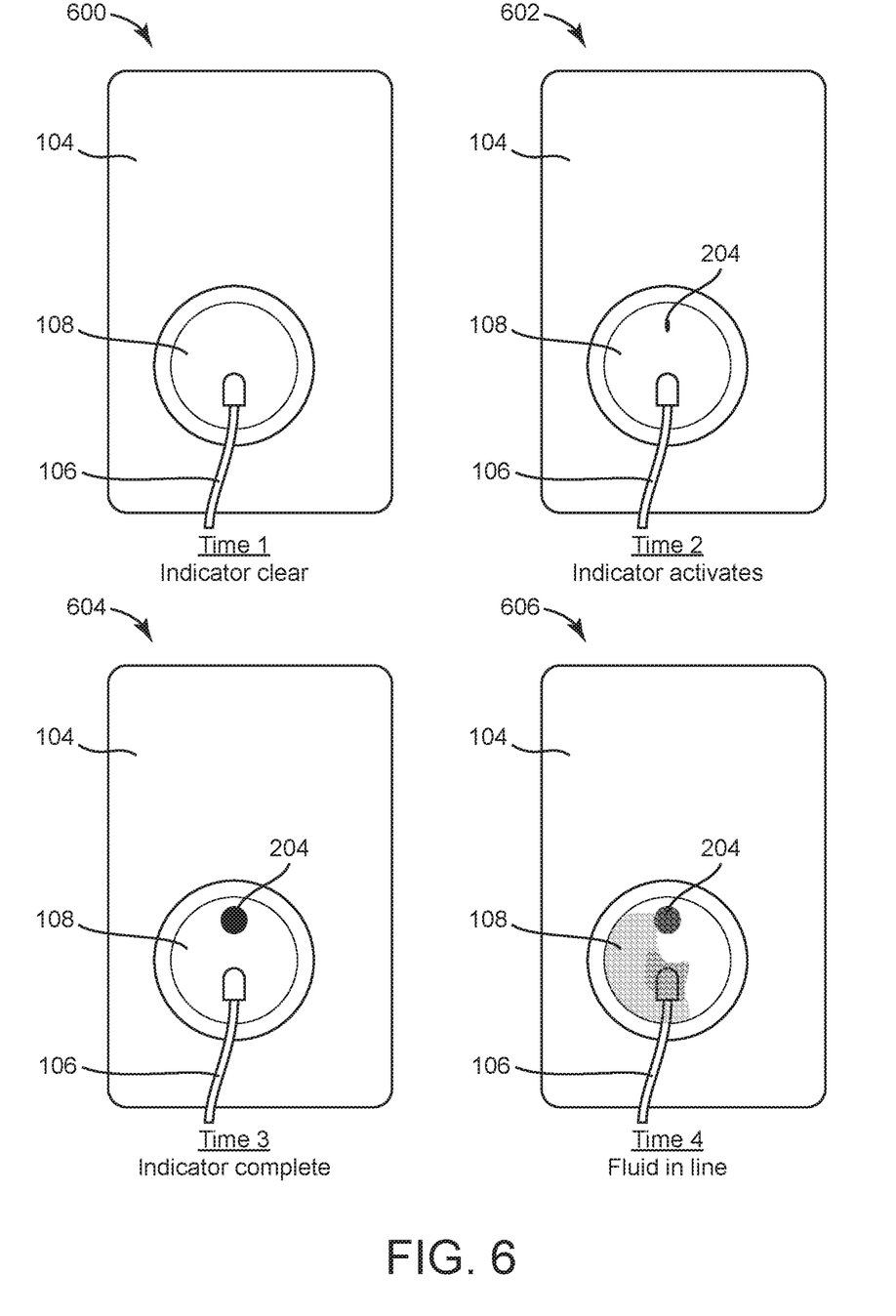
FIG. 6 is series of illustrations depicting release of an indicator dye in the connection assembly of the NPWT system of FIG. 1, according to an exemplary embodiment.

Referring now to FIG. 6, a series of illustrations depicting activation of the fluid-activated indicator 204 as fluid enters the connection assembly 108 is shown, according to an exemplary embodiment. FIG. 6 shows the dressing 104, connection assembly 108, and tube 106 at four points in time, i.e., a first point in time shown in a first frame 600, a second point in time shown in a second frame 602, a third point in time shown in a third frame 604, and a fourth point in time shown in a fourth frame 606.

In the first frame 600, the dressing 104 has absorbed an amount of fluid less than a maximum capacity of the dressing 104, and fluid has not yet crossed the felted foam layer 200 and the hydrophobic film layer 202. Accordingly, the fluid-activated indicator 204 has not been activated and is shown in a pre-activation state. In the example shown, the fluid-activated indicator 204 is substantially the same color as other elements of the dressing 104 in the example of FIG. 4.

As shown in the second frame 602, the dressing 104 has absorbed an amount of fluid approximately equal to the maximum capacity of the dressing 104, and the fluid has started to cross the felted foam layer 200 and the hydrophobic film layer 202 to reach the fluid-activated indicator 204. Accordingly, in the second frame 602, the fluid-activated indicator 204 has started to change color. In the example shown, the fluid-activated indicator 204 is partially changed from a first color that matches other elements of the dressing 104 (e.g., white) to a second color that contrasts with the first color (e.g., red). The change in color of the fluid-activated indicator 204 is visible through the connection pad 206.

At the third frame 604, an amount of fluid sufficient to activate (e.g., change the color of) substantially the entire fluid-activated indicator 204 has been received at the fluid-activated indicator 204. Accordingly, in the third frame 604, the fluid-activated indicator 204 appears as a disk having a color that contrasts with the color(s) of other elements of the dressing 104 and the connection assembly 108.

At the fourth frame 606, fluid has moved from the fluid-activated indicator 204 as shown in the third frame 604 to reach the tube 106. In the embodiment shown, a dye from the fluid-activated indicator 204 has been dispersed (dissolved, carried, etc.) in the fluid, such that the fluid is visible in the color of the dye (e.g., red). In other embodiments, the fluid-activated indicator 204 is omitted, while the natural color of wound exudate in the connection assembly 108 is visible to the user to provide an indication that the dressing. A user is thereby facilitated in viewing the progression of fluid in the connection assembly 108. In some embodiments, a hydrophobic filter is included in the tube 106 and configured to allow airflow through the tube 106 while preventing fluid egress from the tube 106 to the pump 102. In such an embodiment, fluid entry into the connection assembly 108 (e.g., into the volume 213) provides a visual indication that the dressing 104 is full, while the hydrophobic filter in the tube 106 protects the pump 102 from damage and contamination that may otherwise be caused by the fluid.

Figure 7:
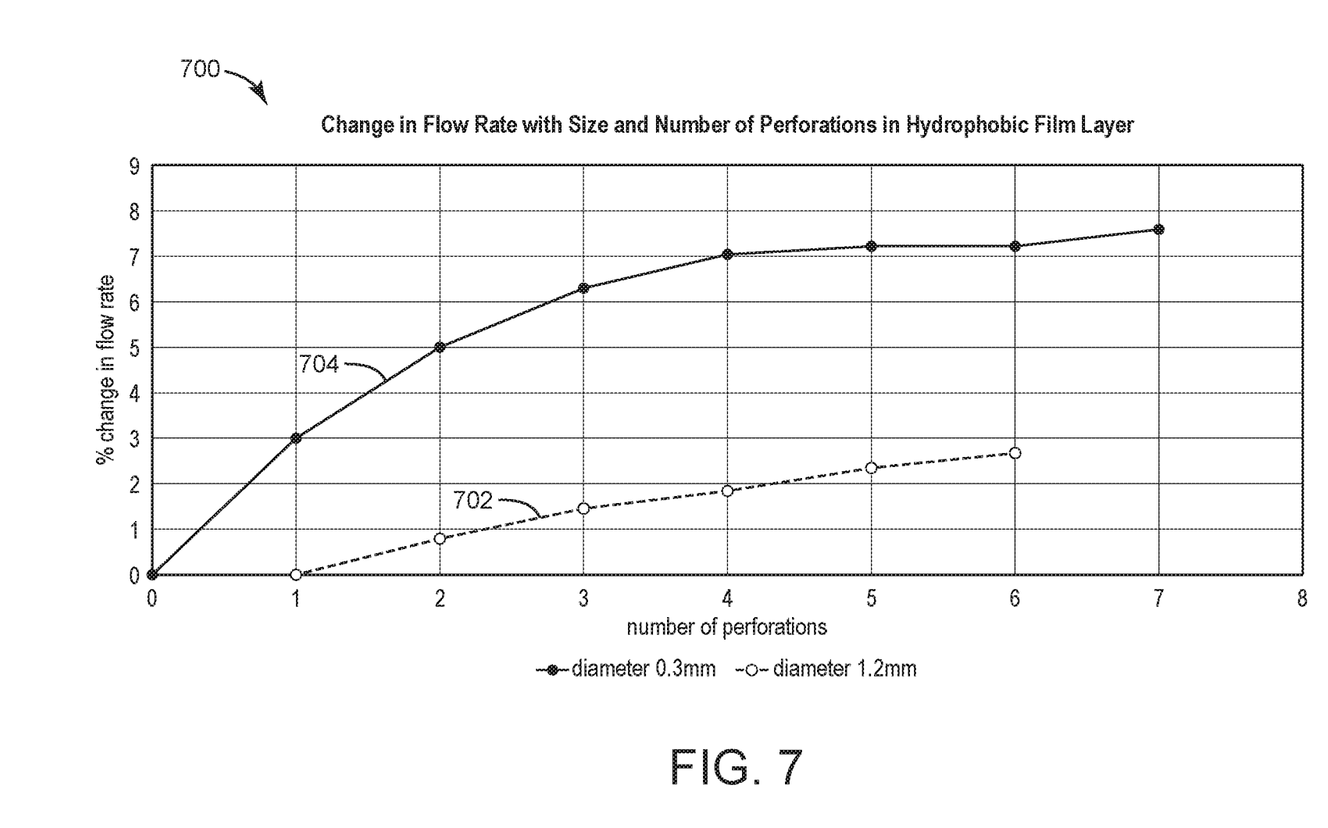
FIG. 7 is a graphical representation of experimental data relating to the NPWT system of FIG. 1.

Referring now to FIG. 7, a graph 700 showing the relative air flow rate through the hydrophobic filter layer 202 of the connection assembly 108 for various numbers of perforations 216 is shown, according to experimental results. In the experiment conducted to generate the data displayed in FIG. 7, a hydrophobic filter layer 202 comprising a hydrophobic micro-filter material marketed as Gore® MMT314 is used. The pump 102 is operated to draw a negative pressure at the dressing 104 of approximately 125 mmHg relative to atmospheric pressure. A first data set, illustrated by line 702, corresponds to an experiment conducted using perforations 216 having diameters of approximately 0.3 millimeters. A second data set, illustrated by the line 704, corresponds to an experiment conducted using perforations 216 having diameters of approximately 1.2 millimeters. Graph 700 illustrates that airflow through the hydrophobic filter layer 202 can be increased by increasing the number and size of perforations 216 through the hydrophobic filter layer 202. Additionally, the line 704 is shown to approximately flatten off after four perforations, showing that in the case of the perforations having diameters of approximately 1.2 millimeters, additional perforations 216 beyond four perforations 216 may have little to no effect on the air flow rate through the hydrophobic filter layer 202. It should be understood that various sizes and numbers of perforations 216 can be selected to customize the rate of air flow through the hydrophobic filter layer 202 and the connection assembly 108.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

Other arrangements and combinations of the elements described herein and shown in the Figures are also contemplated by the present disclosure. The construction and arrangement of the systems and apparatuses as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

What is claimed is:

1. An assembly for coupling a dressing to a tube connected to a pump, the assembly comprising:
    a hydrophobic film layer comprising a perforation extending therethrough;
    an indicator coupled to a first side of the hydrophobic film layer and positioned proximate the perforation;
    a felted foam layer coupled to a second side of the hydrophobic film layer and fluidly communicable with the indicator via the perforation; and
    a connection pad coupled to the first side of the hydrophobic film layer and coupleable to the tube.

2. The assembly of claim 1, wherein the felted foam layer is fluidly communicable with the connection pad via the perforation.

3. The assembly of claim 1, wherein the indicator is configured to change colors in response to contacting fluid.

4. The assembly of claim 3, wherein the indicator comprises a hydrochromic layer comprising a hole extending therethrough, the hole aligned with the perforation.

5. The assembly of claim 3, comprising an adhesive layer configured to couple the indicator to the hydrophobic film layer, and wherein:
    the adhesive layer comprises a channel extending from the perforation to an edge of the indicator; and
    the channel is configured to direct fluid from the perforation to the edge of the indicator.

6. The assembly of claim 1, wherein the hydrophobic film layer is configured to allow the flow of air therethrough from the felted foam layer to the connection pad.

7. A wound therapy system, comprising:
    a wound contact layer configured to contact a wound;
    a manifolding layer coupled to a non-wound-facing side of the wound contact layer;
    a drape coupled to the manifolding layer and sealable over the wound, the drape having a hole extending therethrough;
    a felted foam layer positioned at the hole and fluidly communicable with the manifolding layer;
    a hydrophobic film layer coupled to the felted foam layer and configured to allow air to flow therethrough and substantially prevent liquid from flowing therethrough, the hydrophobic film layer having a perforation extending therethrough, the perforation configured to allow liquid to pass through the hydrophobic film layer;
    a fluid-activated indicator coupled to the hydrophobic film layer proximate the perforation, the hydrophobic film layer positioned between the fluid-activated indicator and the felted foam layer;
    a connection pad coupled to the drape and sealed over the hole, the felted foam layer, the hydrophobic film layer, and the indicator;
    a tube coupled to the connection pad; and
    a pump coupled to the tube, the pump operable to draw a negative pressure at the wound by removing air from the manifolding layer via the felted foam layer, the hydrophobic film layer, the connection pad, and the tube.

8. The wound therapy system of claim 7, wherein the felted foam layer is fluidly communicable with the connection pad via the perforation.

9. The wound therapy system of claim 7, wherein the fluid-activated indicator is configured to change colors in response to contacting fluid.

10. The wound therapy system of claim 9, wherein the fluid-activated indicator comprises a hydrochromic layer comprising a hole extending therethrough, the hole aligned with the perforation.

11. The wound therapy system of claim 9, comprising an adhesive layer configured to couple the indicator to the hydrophobic film layer, and wherein:
    the adhesive layer comprises a channel extending from the perforation to an edge of the indicator; and
    the channel is configured to direct fluid from the perforation to the edge of the indicator.

12. The wound therapy system of claim 7, wherein the connection pad is transparent or translucent such that the indicator is visible through the connection pad.

13. A method for manufacturing a wound therapy system, comprising:
    coupling an indicator to a hydrophobic film layer;
    creating a perforation through the indicator and the hydrophobic film layer;
    coupling the hydrophobic film layer to a felted foam layer, the hydrophobic film layer positioned between the indicator and the felted foam layer; and
    coupling a connection pad to the hydrophobic film layer, the connection pad in fluid communication with the felted foam layer via the perforation.

14. The method of claim 13, comprising coupling the connection pad to a tube.

15. The method of claim 13, comprising:
    forming a hole through a drape;
    coupling the connection pad to the drape at the hole;
    coupling a manifolding layer to the drape, the manifolding layer fluidly communicable with the felted foam layer via the hole; and
    coupling a wound contact layer to the manifolding layer.

16. The method of claim 15, comprising:
    coupling the connection pad to a tube; and
    coupling the tube to a pump, the pump configured to draw a negative pressure at the manifolding layer.

17. The method of claim 13, wherein the indicator comprises a hydrochromic layer configured to change color when the hydrochromic layer contacts fluid.

18. The method of claim 13, wherein coupling the indicator to a hydrophobic film layer comprises providing an adhesive layer between the indicator and the hydrophobic film layer.

19. The method of claim 18, comprising providing the indicator with a channel extending from the perforation to an edge of the indicator.

20. The method of claim 13, comprising creating a plurality of additional perforations through the hydrophobic film layer.

* * * * *